United States Patent

Lai

[19]

[11] Patent Number: 5,824,617
[45] Date of Patent: *Oct. 20, 1998

[54] LOW ALKALINE INVERTED IN-SITU CRYSTALLIZED ZEOLITE MEMBRANE

[75] Inventor: Wenyih Frank Lai, Fair Lawn, N.J.

[73] Assignee: Exxon Research & Engineering Company, Florham Park, N.J.

[ * ] Notice: The terminal 14 months of this patent has been disclaimed.

[21] Appl. No.: 267,760

[22] Filed: Jul. 8, 1994

[51] Int. Cl.⁶ ...................................................... B01J 20/28
[52] U.S. Cl. .................................. 502/4; 502/64; 502/66; 502/71; 502/77
[58] Field of Search .................................. 502/4, 64, 66, 502/71, 77

[56] References Cited

U.S. PATENT DOCUMENTS

| | | | |
|---|---|---|---|
| 3,244,643 | 4/1966 | Schwartz | 252/455 |
| 4,571,443 | 2/1986 | DiCosimo et al. | 585/428 |
| 4,631,267 | 12/1986 | Lachman et al. | 502/439 |
| 4,631,268 | 12/1986 | Lachman et al. | 502/439 |
| 4,631,269 | 12/1986 | Lachman et al. | 502/439 |
| 4,657,880 | 4/1987 | Lachman et al. | 502/64 |
| 4,699,892 | 10/1987 | Suzuki | 502/4 |
| 4,716,136 | 12/1987 | Weisz et al. | 502/64 |
| 4,800,187 | 1/1989 | Lachman et al. | 502/64 |
| 4,827,071 | 5/1989 | Hazbun | 585/443 |
| 4,860,584 | 8/1989 | Mercer et al. | 73/336.5 |
| 4,876,890 | 10/1989 | Mercer et al. | 73/336.5 |
| 4,904,518 | 2/1990 | Mercer et al. | 428/195 |
| 4,925,459 | 5/1990 | Rojey et al. | 155/16 |
| 4,927,768 | 5/1990 | Coughlin et al. | 436/172 |
| 4,968,430 | 11/1990 | Hildebrand et al. | 210/640 |
| 4,973,606 | 11/1990 | Sterzel et al. | 521/27 |
| 4,981,676 | 1/1991 | Minet et al. | 423/652 |
| 4,990,714 | 2/1991 | Nemet-Mavrodin | 585/407 |
| 5,019,263 | 5/1991 | Haag et al. | 210/500.25 |
| 5,100,596 | 3/1992 | Haag et al. | 264/42 |
| 5,110,478 | 5/1992 | Haag et al. | 210/650 |
| 5,143,614 | 9/1992 | Soria et al. | 210/321.61 |
| 5,258,339 | 11/1993 | Ma et al. | 502/4 |
| 5,260,242 | 11/1993 | Dunne et al. | 502/63 |
| 5,266,542 | 11/1993 | Hashimoto et al. | 502/64 |

FOREIGN PATENT DOCUMENTS

| | | |
|---|---|---|
| 1235684 | 4/1988 | Canada . |
| 2016960AA | 11/1990 | Canada . |
| 1040152 | 3/1990 | China . |
| 0135069A2 | 3/1985 | European Pat. Off. . |
| 0180200A2 | 5/1986 | European Pat. Off. . |
| 0188182A1 | 7/1986 | European Pat. Off. . |
| 0228885A2 | 7/1987 | European Pat. Off. . |

(List continued on next page.)

OTHER PUBLICATIONS

Synthesis and characterization of a pure zeolitic membrane, Tsikoyiannis and Haag, Zeolites, 1992, vol. 12, Feb., pp. 126–130.

*Primary Examiner*—Steven Bos
*Assistant Examiner*—Thomas G. Dunn, Jr.
*Attorney, Agent, or Firm*—Esteile C. Bakun; Jay Simon

[57] ABSTRACT

Applicant has discovered a new zeolite membrane and a process for preparing the same. The membrane is unique in that the zeolite crystals making up the membrane pack in a manner such that the membrane is essentially continuous with no large scale voids even when the membrane is <10 μm thick. Thus, the present invention is directed toward a zeolite membrane wherein said membrane is comprised of a porous substrate and a layer of zeolite crystals wherein said layer of zeolite crystals is a polycrystalline layer with at least 99% of said zeolite crystals having at least one point between adjacent crystals that is $\leq 20$ Å and wherein at least 90% of said crystals have widths of from about 2 to about 50 microns and wherein at least 75% of said crystals have a thickness of within 20% of the average crystal thickness and wherein said membrane has at most 1 V % voids in said zeolite layer.

17 Claims, 4 Drawing Sheets

FOREIGN PATENT DOCUMENTS

| | | |
|---|---|---|
| 0324675A1 | 7/1989 | European Pat. Off. . |
| 0336241A2 | 10/1989 | European Pat. Off. . |
| 0344011A1 | 11/1989 | European Pat. Off. . |
| 0398093A2 | 11/1990 | European Pat. Off. . |
| 0442410A1 | 8/1991 | European Pat. Off. . |
| 0460512A1 | 12/1991 | European Pat. Off. . |
| 0476363A1 | 3/1992 | European Pat. Off. . |
| 0481658A1 | 4/1992 | European Pat. Off. . |
| 0481659A1 | 4/1992 | European Pat. Off. . |
| 0481660A1 | 4/1992 | European Pat. Off. . |
| 0511739A1 | 11/1992 | European Pat. Off. . |
| 0536995A1 | 4/1993 | European Pat. Off. . |
| 0570842A1 | 11/1993 | European Pat. Off. . |
| 2079460 | 11/1971 | France . |
| 3827049 | 2/1990 | Germany . |
| 4029433 | 3/1992 | Germany . |
| 63287504 | 11/1984 | Japan . |
| 60-28826 | 3/1985 | Japan . |
| 60-129119 | 7/1985 | Japan . |
| 3-262523 | 11/1991 | Japan . |
| 2190397 | 11/1987 | United Kingdom . |
| WO9213631 | 8/1992 | WIPO . |
| WO9219574 | 11/1992 | WIPO . |
| WO9300155 | 1/1993 | WIPO . |
| WO9317781 | 9/1993 | WIPO . |
| WO9319840 | 10/1993 | WIPO . |
| WO9319841 | 10/1993 | WIPO . |
| WO9401209 | 1/1994 | WIPO . |
| WO9401365 | 1/1994 | WIPO . |

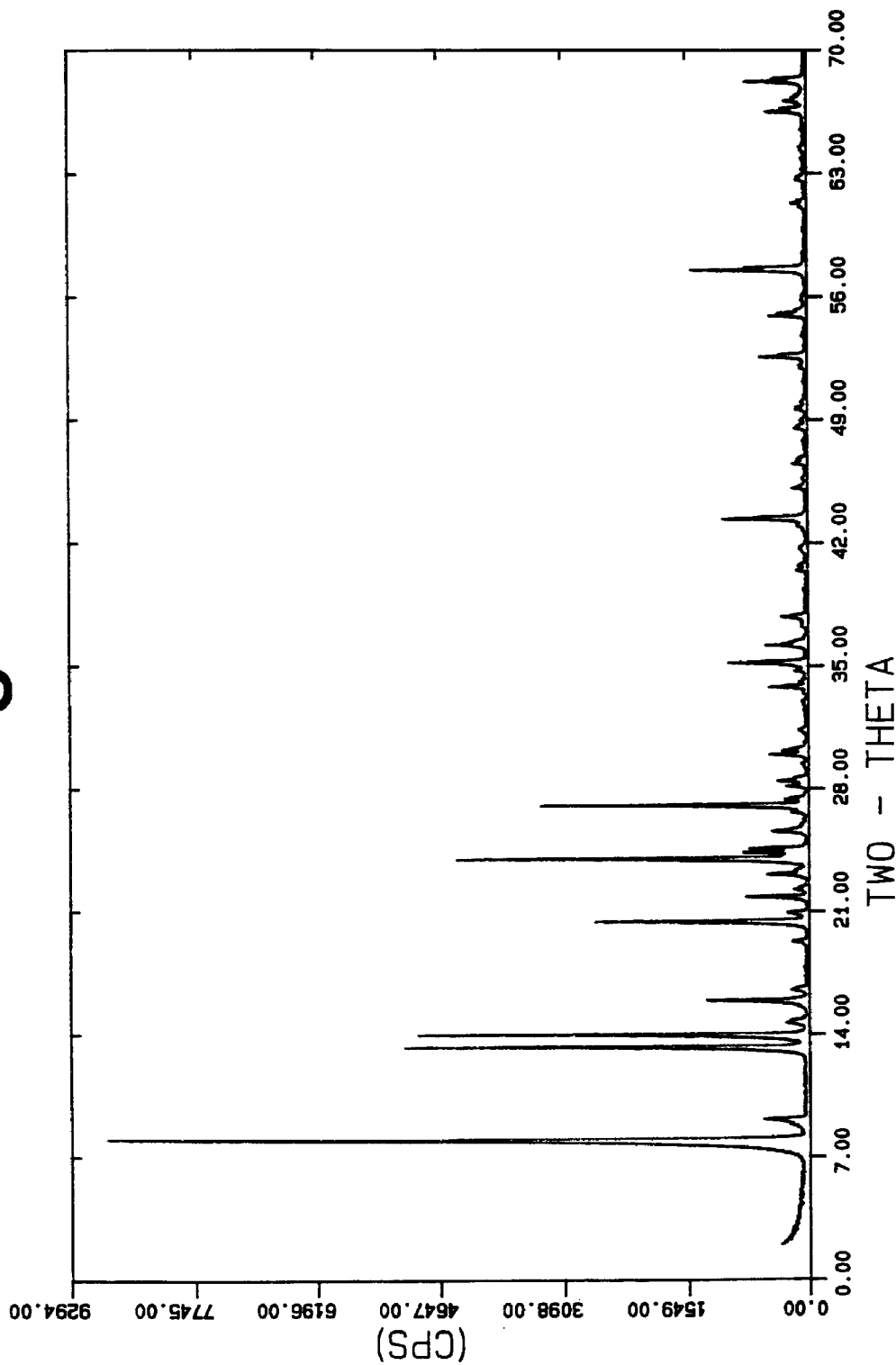

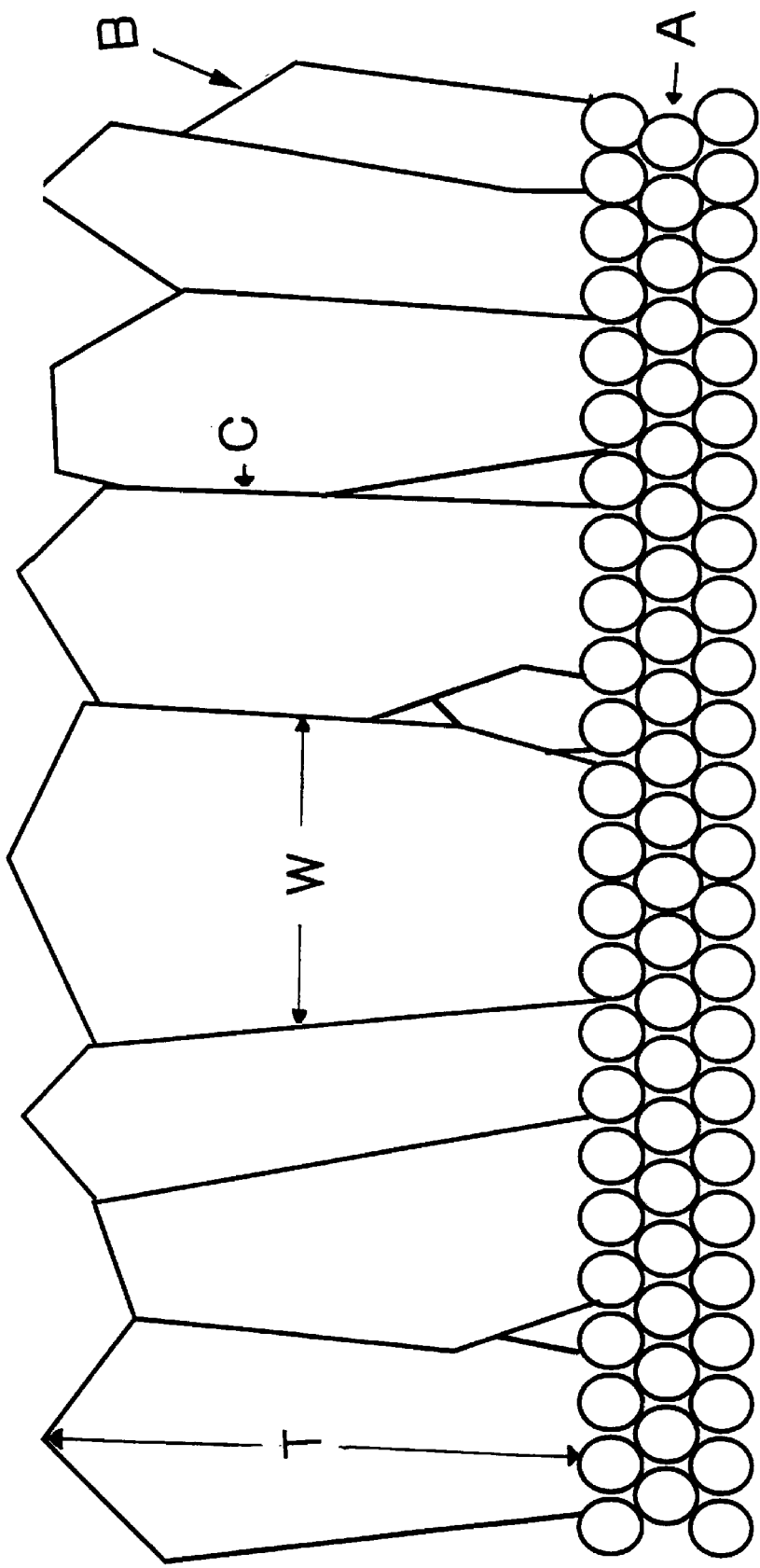

LOW ALKALINE INVERTED IN-SITU CRYSTALLIZED ZEOLITE MEMBRANE

FIELD OF THE INVENTION

The present invention is related to a new zeolite membrane.

BACKGROUND OF THE INVENTION

U.S. Pat. No. 5,110,478 describes the direct synthesis of zeolite membranes. The membranes produced in accordance with the teachings of U.S. Pat. No. 5,110,478 were discussed in "Synthesis and Characterization of a Pure Zeolite Membrane," J. G. Tsikoyiannis and W. Haag, Zeolites (Vol. 12, p. 126, 1992). Such membranes are free standing and are not affixed or attached as layers to any supports. Furthermore, the membranes have a gradient of crystal sizes across the thickness of the membrane. Such a gradient precludes growth of a thin membrane with a minimum number of nonselective permeation paths.

Zeolite membranes have also been grown on supports. See e.g. "High temperature stainless steel supported zeolite (MFI) membranes: Preparation, Module, Construction and Permeation Experiments, " E. R. Geus, H. vanBekkum, and J. A. Moulÿin, Microporous Materials, Vol. 1, p. 137, 1993; Netherlands Patent Application 91011048; European Patent Application 91309239.1 and U.S. Pat. No. 4,099,692.

All of the above prepared membranes have nonuniform sized zeolite crystals and are noncontinuous, exhibiting many voids. Obtaining functional zeolite membranes from low alkaline synthesis routes is difficult because the heterogeneous crystals in the membrane require an enormous membrane thickness to seal pinholes and void structures which lower the membrane selectivity.

BRIEF DESCRIPTION OF THE DRAWINGS

FIG. 3 is an X-ray diffraction pattern showing the preferred orientation in low alkaline inverted membranes. The x-axis is 2θ and the y-axis is intensity in CPS.

FIG. 4 is a schematic view of a zeolite layer on a porous substrate. (A) is the porous substrate, (B) the zeolite layer, (C) a grain boundary, (W) the width at one point along a zeolite crystal, and (T) the thickness of one crystal.

SUMMARY OF THE INVENTION

Figure 1:
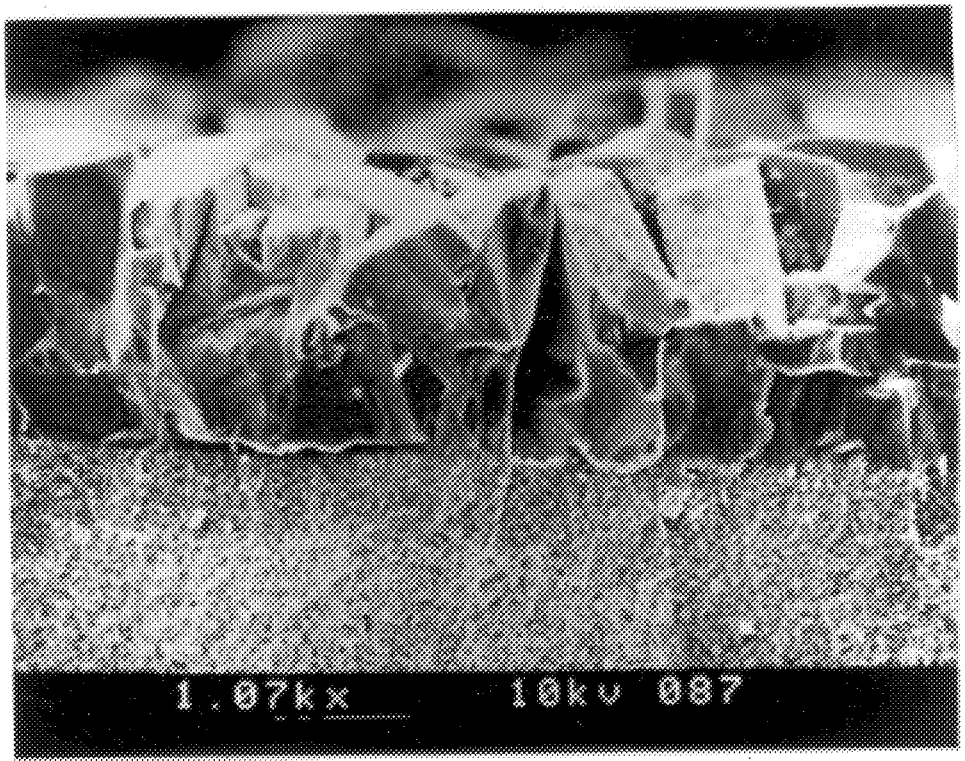
FIG. 1 is an electron micrograph showing a cross-sectional view of a zeolite layer grown on the inverted face of a porous a alumina substrate.
Figure 2:
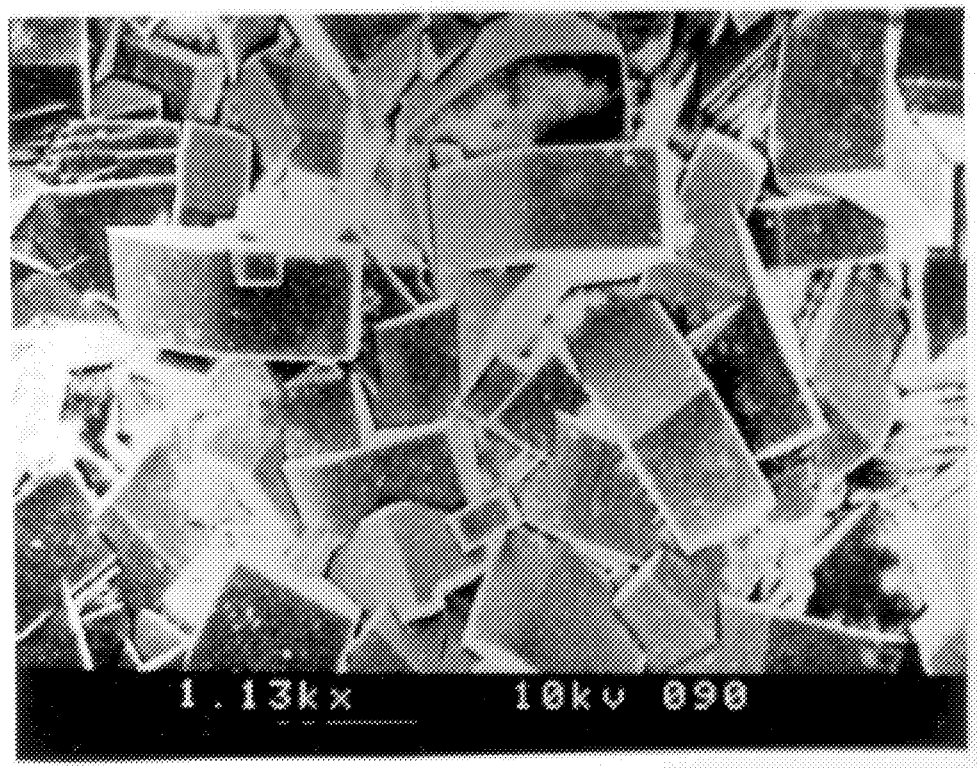
FIG. 2 is an electron micrograph of a top view of a zeolite layer grown on the inverted face of a porous α alumina substrate.

Applicant has discovered a new zeolite membrane and a process for preparing the same. The membrane is unique in that the zeolite crystals making up the membrane pack in a manner such that the membrane is essentially continuous with no large scale voids even when the membrane is <10 μm thick.

Hence, one aspect of the present invention is directed toward a zeolite membrane comprised of a substrate and a layer of zeolite crystals wherein said layer of zeolite crystals is a polycrystalline layer with at least 99% of said zeolite crystals having at least one point between adjacent crystals that is $\leq 20$ Å and wherein at least 90% of said zeolite crystals have widths of from about 2 to about 50 microns and wherein at least 75% of said zeolite crystals have a thickness of within 20% of the average crystal thickness and wherein said membrane has at most 1 V % voids in said zeolite layer.

Another aspect of the present invention is directed toward a process of making a zeolite membrane on a porous support comprising the steps of:

(a) immersing a substrate onto which a zeolite layer is to be grown, in a zeolite synthesis mixture;

(b) autoclaving said substrate and said zeolite synthesis mixture for a time and at a temperature sufficient to form a zeolite layer on said substrate and wherein settling of particles produced from said zeolite synthesis mixture during autoclaving, onto said zeolite layer is prevented;

(c) washing said substrate having said zeolite layer thereon with a solution comprising water for a time and at a temperature sufficient to remove any unreacted zeolite synthesis mixture to form a membrane.

The process further comprises calcining said membrane of step (c) at a temperature of about 400° to about 600° C. for at least about 10 minutes when said zeolite synthesis mixture contains an organic template.

The zeolite membranes thus produced are useful for size exclusion separations such as separation of dye molecules from alcohol and oligomer separation from hexane.

DETAILED DESCRIPTION OF THE INVENTION

Applicant has discovered a new zeolite membrane comprised of a polycrystalline zeolite layer on a support. The support can be porous or non-porous, preferably porous supports will be used. The zeolite layer can be grown on any porous supports including but not limited to alumina, titania, cordierite, mullite, stainless steel, pyrex, silica, silicon carbide, silicon nitride, carbon, graphite and mixtures thereof. Additionally, non-porous supports will include quartz, silicon, glass, borosilicate glasses, dense ceramics, i.e., clays, metals, polymers, graphite and mixtures thereof. When non-porous supports are utilized, the membranes are useful as sensors.

Growth of the zeolite layer is carried out by immersing the substrate in a zeolite synthesis mixture for a time and at a temperature sufficient to effect crystallization. For example, in an autoclave under autogenous pressure. Immersion of the substrate must be carried out such that there is no settling of crystals formed in the synthesis mixture during autoclaving onto the substrate. The synthesis mixture may thus be handled in a manner to prevent such settling.

In a preferred embodiment, the zeolite layer is grown on a support which is inverted in the zeolite synthesis mixture. Inverted as used herein means that the zeolite layer is grown on the side of the substrate oriented from 90 to 270 degrees in the synthesis mixture. In the 180 degree orientation, the side of the substrate onto which the zeolite layer is grown, is horizontal and facing downward. This is referred to as inverted. Preferably, the membrane will be grown on the 180 degree oriented side. The surface of the substrate to be coated should be at least 5 mm, from the bottom and sides of the vessel containing the zeolite synthesis mixture, preferably at least 8 mm at its lowest point during the process of preparation. Applicant believes that inversion of the substrate prevents zeolite crystals, which are homogeneously nucleated in the zeolite synthesis mixture, from settling onto the substrate where the zeolite layer is grown. Thus, the crystals do not incorporate into the growing zeolite layer or perturb the growth process. Hence, at least 99%, preferably at least 99.9% of the crystals in the zeolite layer have at least one point between adjacent zeolite crystals that is ≦20Å. In the instant invention, the spacing between adjacent crystals is set by a grain boundary zone and the maximum grain boundary zone, absent voids or defects, will be ≦40Å. Additionally, at least 90%, preferably at least 95% of the zeolite crystals in the zeolite layer have widths of from about 2 to about 50 microns. As used herein, grain boundary zone is the width of the disordered zone between two adjacent ordered crystals. The zeolite crystals in the zeolite layer are intergrown in the membrane so that nonselective permeation paths through the membrane are blocked by the narrowest point of approach between crystals. Non-selective permeation pathways are taken to be permeation pathways which exist at room temperature that do not pass through the zeolite crystals. This blockage of non-permeation pathways exists at room temperature after a template which occludes the pore structure is removed from the zeolite crystals. Templates which are used to grow the zeolite are often removed by a calcination step. From transmission electron microscopy (TEM) the narrowest point of approach between crystals of less than 20 Å after the template is removed is established. The space between crystals at this point can contain inorganic oxide material that restricts non-selective permeation of molecules through the membrane. The absence of non-selective permeation paths can be detected by the ability to prevent the permeation at room temperature (~20° C.) of dye molecules through the membrane after any template is removed from the pore structure. Dye molecules which can be chosen to detect non-selective permeation pathways through the membrane should have minimum dimensions which are larger than the controlling aperture through the zeolite and the size of the dye molecule should also be less than 20 Å. Non-selective pathways transport dye molecules which are larger than the pore size of the zeolite. The dye molecules should be carried in a solution made with a solvent which can be transported through the zeolite pore structure and the zeolite layer should not be allowed to pick up foreign contaminants (such as water) before being tested. It is found that the zeolite membranes made in accordance with the present invention block the permeation of dye molecules at room temperature through the zeolite layer. All of the dye molecules chosen have sizes less than 20 Å. The lack of permeation at room temperature of dye molecules with sizes less than ~20 Å demonstrates that non-selective permeation pathways with sizes less than ~20 Å are blocked. It should be noted that this test does not have to be performed with a dye molecule and any molecular species that can be detected having a size less than 20 Å and greater than the zeolite pore dimension can be used. The advantage of using a dye molecule is that it can be readily detected by optical means.

MFI zeolite membranes grown in accordance with the instant invention preferably display a degree of C-orientation (within 30° of the normal to the surface of the substrate in the zeolite layer). More especially, the longest edges (thickness) of at least 75% of the crystals are within 30° of perpendicular to the layer plane, advantageously at least 90% of the crystals being within that angle.

A measure of the proportion of the crystals that have the longest axis (thickness) normal to the plane of the layer may be obtained by comparison of the X-ray diffraction pattern of the layer with that of a randomly oriented zeolite powder. In the case of an MFI-type zeolite, for example, the longest edge corresponding to the c axis, the ratio of the intensity of the 002-peak to the combined 200 and 020 peak is divided by the same ratio for randomly oriented powder; the quotient is termed the crystallographic preferred orientation (CPO).

Measured in this way, zeolite layers in accordance with the invention have a CPO of at least 1, and may have a CPO as high as 500. The crystals in the zeolite layer range in thickness from about 5 to 100μ, preferably about 30 to about 60μ, most preferably about 30μ. Although the crystals may range in thickness from 5 to 100μ, for any given membrane, 75 V %, preferably 90 V % of the crystals will all have crystal thicknesses of within 20% of the average crystal thickness. Thickness is herein defined as the length of the crystals from the substrate surface to the uppermost edge of the zeolite layer perpendicular to the substrate. Membranes made from zeolites other than MFI will also display a degree of orientation, however, such orientation may not be in the c direction.

The instant membranes are virtually free of voids. They exhibit at most about 1 Volume % voids, preferably less than 0.5 Volume % voids.

Void as used herein means spaces between the zeolite crystals in the zeolite layer along grain boundaries larger than 40 Å. Defects are spaces between adjacent zeolite crystals extending through the thickness of the zeolite layer. In the instant membrane, the total number of defects in the zeolite layer with sizes >40Å is <10,000 per square inch, preferably <100 per square inch. The number of defects having spacing between adjacent zeolite crystals larger than about 2000 Å is <100/inch$^2$, preferably <0.1/inch$^2$. Voids and defects can be detected from cross-sectional images of the zeolite layer made in the scanning or transmission electron microscope.

Defects of the type described can be detected in dye permeation experiments. Isolated points at which dye permeates into the substrate reveal such defects. Defects can also be determined by examining cross-sections of the zeolites membrane in the scanning electron microscope. Gas permeation can also be used to reveal defects in the membrane. If the permeability of the zeolite layer to nitrogen at room temperature is less than $5 \times 10^{-6}$ moles/(m$^2$-sec-Pascal) for each micron of thickness of the zeolite layer, the membrane can be considered to have an acceptable defect density. More preferably, the permeability of the zeolite layer to nitrogen at room temperature is less than $5 \times 10^{-7}$ moles/m$^2$-sec-Pascal) for each micron of thickness of the zeolite layer. The zeolite membranes of the instant invention are prepared from zeolite synthesis mixtures. Zeolite synthesis mixtures are any mixtures from which zeolite crystals are grown and are well known in the art. (See, e.g., *Handbook of Molecular Sieves*, Rosemary Szostak, Van Nostrand Reinhold, NY, 1992 and *Zeolite Molecular Sieves*, D. W. Breck, R. E. Kreiger Publishing Co., Malabar, Fl. 1984, ISBN 0-89874-648-5). For example, for MFI zeolites, the synthesis mixture can be a mixture having a pH of about 8 to about 12 and is readily prepared by those skilled in the art. For example, suitable mixtures include Na$_2$O, TPABr (tetrapropyl ammonium bromide), SiO$_2$ and water. The membranes are grown by suspending the porous support material of choice in the zeolite synthesis mixture. The synthesis mixture is then heated to about 50° to about 300° C., preferably about 100° to about 250° C., preferably about 180° C. for a period of about 30 minutes to about 300 hours. Any undesired growth on the substrate can be easily removed by known techniques. For example, grinding can be used.

The zeolite membranes which can be prepared in accordance with the instant invention include silicates, aluminosilicates, aluminophosphates, silicoaluminophosphates, metalloalumino-phosphates, stanosilicates and mixtures thereof. Representative examples of such zeolites are MFI, FAU (including zeolite x, zeolite y), zeolite beta, MAZ, LTA, LTL, CHA, AFI, AEL, BEA, EUO, FER, KFI, MOR, MEL, MTW, OFF, TON, AFS, AFY, APC, APD, MTN, MTT, AEL and mixtures thereof, preferably MFI zeolite with a silicon to aluminum ratio greater than 30 will be used including compositions with no aluminum. MFI zeolites with Si/Al ratios greater than 30 are herein referred to as silicalite.

Some of the above materials while not being true zeolites are frequently referred to in the literature as such, and this term will be used herein to include such materials.

The substrate on which the zeolite layer is grown may be porous or non-porous. If the substrate is porous, it will be a porous material throughout its entire thickness. Preferably an inorganic oxide or stainless steel will be utilized. The porous substrate, hence can be a ceramic, metal, carbide, polymer or mixture thereof. For example, alumina, titania, cordierite, mullite, stainless steel, pyrex, silica, silicon carbide and silicon nitride or mixture thereof can be utilized as porous substrates. The porous substrate, hence may have a uniform pore size throughout or may be asymmetrical, having a larger pore structure throughout the bulk of the substrate with a smaller pore structure at the surface on which the zeolite layer is to be grown. The substrate pore size is dictated by mass transfer considerations. It is preferred that the pore structure and thickness of the substrate be chosen such that the mass transfer resistance does not limit the flux of material permeating through the zeolite membrane during use. The porous substrate will hence display a porosity of about 5 to about 70%, preferably about 20 to about 50% and an average pore size of about 0.004 to about 100$\mu$, preferably about 0.05 to about 2 microns.

It is preferred that the surface of the substrate, porous or non-porous, on which the zeolite layer is grown be smooth. Roughness in the substrate leads to defects in the membrane. The substrate should have an average roughness with an amplitude of less than 10 $\mu$m with an aspect ratio of the roughness less than 1:1. It is preferable that the average roughness of the substrate be less 0.5 $\mu$m with an aspect ratio of the roughness less than 1:1. Though non-porous substrates may be utilized, porous substrates are preferred.

Once the zeolite layer has been grown, the substrate, with attached layer, is washed with water for a time and at a temperature sufficient to remove any zeolite synthesis mixture which did not react during autoclaving. Hence, washing may be conducted at a temperature of about 15° to 100° C., preferably about 80° to about 100° C., for at least 10 minutes, preferably at least six hours. Excess washing for longer periods will not affect the membranes separation capabilities.

Once washed, if the zeolite synthesis mixture contained an organic template, the membrane is calcined at about 400° to 600° C. for at least one hour, preferably at least about six hours. Longer calcination times will not affect the performance of the membrane.

Separations which may be carried out using a membrane in accordance with the invention include, for example, separation of normal alkanes from co-boiling hydrocarbons, for example normal alkanes from iso alkanes such as $C_4$ to $C_6$ mixtures and n-$C_{10}$ to $C_{16}$ alkanes from kerosene; separation of aromatic compounds from one another, especially separation of $C_8$ aromatic isomers from each other, more especially para-xylene from a mixture of xylenes and, optionally, ethylbenzene, and separation of aromatics of different carbon numbers, for example, mixtures of benzene, toluene, and mixed $C_8$ aromatics; separation of aromatic compounds from aliphatic compounds, especially aromatic molecules with from 6 to 8 carbon atoms from $C_5$ to $C_{10}$ (naphtha range) aliphatics; separation of olefinic compounds from saturated compounds, especially light alkenes from alkane/alkene mixtures, more especially ethene from ethane and propene from propane; removing hydrogen from hydrogen-containing streams, especially from light refinery and petrochemical gas streams, more especially from $C_2$ and lighter components; and alcohols from aqueous streams; alcohols from other hydrocarbons, particularly alkanes and alkenes that may be present in mixtures formed during the manufacture of alcohols and separation of heteroatomic compounds from hydrocarbons such as alcohols and sulphur containing materials such as $H_2S$ and mercaptans. The zeolite layer of the invention may be employed as a membrane in such separations without the problem of being damaged by contact with the materials to be separated. Furthermore, many of these separations are carried out at elevated temperatures, as high as 500° C., and it is an advantage of the supported layer of the present invention that it may be used at such elevated temperatures.

The present invention accordingly also provides a process for the separation of a fluid mixture which comprises contacting the mixture with one face of a layer according to the invention in the form of a membrane under conditions such that at least one component of the mixture has a different steady state permeability through the layer from that of another component and recovering a component or mixture of components from the other face of the layer.

The invention further provides a process for catalysing a chemical reaction which comprises contacting a feedstock with a layer according to the invention which is in active catalytic form under catalytic conversion conditions and recovering a composition comprising at least one conversion product.

The invention further provides a process for catalysing a chemical reaction which comprises contacting a feedstock with one face of a layer according to the invention, that is in the form of a membrane and in active catalytic form, under catalytic conversion conditions, and recovering from an opposite face of the layer at least one conversion product, advantageously in a concentration differing from its equilibrium concentration in the reaction mixture. For example, a p-xylene rich mixture from the reactor or reactor product in a xylenes isomerization process; aromatic compounds from aliphatics and hydrogen in a reforming reactor; hydrogen removal from refinery and chemicals processes such as alkane dehydrogenation in the formation of alkenes, light alkane/alkene dehydrocyclization in the formation of aromatics (e.g., Cyclar), ethylbenzene dehydrogenation to styrene. The invention further provides a process for catalysing a chemical reaction which comprises contacting one reactant of a bimolecular reaction with one face of a layer according to the invention, that is in the form of a membrane and in active catalytic form, under catalytic conversion conditions, and controlling the addition of a second reactant by diffusion from the opposite face of the layer in order to more precisely control reaction conditions. Examples include controlling ethylene, propylene or hydrogen addition to benzene in the formation of ethylbenzene, cumene or cyclohexane, respectively.

Catalytic functions can be incorporated into the membranes. When a catalytic function is incorporated into the membrane, it can be used as an active element in a membrane reactor. Several different membrane reactor architectures can be constructed depending on the location of the catalytic site in the membrane. In one case the catalytic function can be located within the zeolite layer, while in another case the catalytic function can be located within the support, and in another case the catalytic function can be distributed throughout the support and the zeolite layer. In addition, catalytic function can be incorporated into a membrane reactor by locating conventional catalyst particles near one or more surfaces of the membrane such that specific products or reactants are continuously and selectively removed or added to the reaction zone throughout the membrane reactor. Impregnating with catalytically active metals such as Group VIII noble metals, e.g. Pt, can impart the catalytic function to the membrane. The catalytically active metals can be incorporated by techniques known in the art such as incipient wetness. The amount of Group VIII noble metal to be incorporated will range from about 0.01 to about 10 wt %.

Some specific reaction systems where these membranes would be advantageous for selective separation either in the reactor or on reactor effluent include: selective removal of a para-xylene rich mixture from the reactor, reactor product, reactor feed or other locations in a xylenes isomerization process; selective separation of aromatics fractions or specific aromatics molecule rich streams from catalytic reforming or other aromatics generation processes such as light alkane and alkene dehydrocyclization processes (e.g., $C_3$–$C_7$ paraffins to aromatics from processes such as Cyclar), methanol to gasoline and catalytic cracking processes; selective separation of benzene rich fractions from refinery and chemical plant streams and processes; selective separation of olefins or specific olefin fractions from refinery and chemicals processing units including catalytic and thermal cracking, olefins isomerization processes, methanol to olefins processes, naphtha to olefins conversion processes, alkane dehydrogenation processes such as propane dehydrogenation to propylene; selective removal of hydrogen from refinery and chemicals streams and processes such as catalytic reforming, alkane dehydrogenation, catalytic cracking, thermal cracking, light alkane/alkene dehydrocyclization, ethylbenzene dehydrogenation, paraffin dehydrogenation; selective separation of molecular isomers in processes such as butane isomerization, paraffin isomerization, olefin isomerization, selective separation of alcohols from aqueous streams and/or other hydrocarbons.

The following examples are for illustration and are not meant to be limiting.

EXAMPLES

1. Materials

The hydrothermal experiments were performed using mixtures of the following reagents: NaOH (Baker), Al($NO_3$)$_3$, 9$H_2$O(Baker), Ludox AS-40 (Dupont), tetrapropylammonium bromide (98%, Aldrich), and distilled water.

Porous alumina and stainless steel substrates were used for the support of the zeolite layers. The average pore size and porosity of the alumina substrate was about 800Å and 32%, respectively. Porous sintered stainless steel substrates from Mott's (0.25 $\mu$m) and Pall (M020, 2 $\mu$m) were obtained. All of the substrates were cleaned with acetone in an ultra-sonic bath, dried at 120° C. and then cooled down to room temperature before use.

2. Hydrothermal Reaction

MFI membranes were prepared from two different reaction batch mixtures, one contained silica only to make high silica MFI and the other with added alumina to make ZSM-5. They have the general formulation x $M_2$O:10 $SiO_2$: z $Al_2O_3$:pTPABr:y $H_2O$; M can be Na, K, Rb, & Cs, x varied from 0.1 to 0.5, and y varied from 50 to 3000, z varied from 0 to 0.15 and p varied from 0.2 to 1. All the results shown in the next section have the composition of 0.22 $Na_2O$:10 $SiO_2$:0$Al_2O_3$:280 $H_2O$:0.5 TPABr (tetrapropylammoniumbromide) with the exception of the ZSM-5 sample which contained 0.05 $Al_2O_3$. The 1.74 g or TPABr and 0.45 g of NaOH (50 wt %) were dissolved in 52 ml of distilled water with stirring. To this solution, 18.8 g of Ludox AS-40 was then added with agitation for at least 15 minutes until a uniform solution was formed.

The substrates were placed inverted (180 degree orientation) in a Teflon lined reaction vessel supported on a stainless steel wire frame. The distance between the substrate and the bottom of reactor was at least 5 mm. The synthesis solution was then poured into the reactor to cover the whole substrate. The autoclave was sealed and placed in an oven, which was preheated at the desired temperature. The reaction bombs were removed from the oven after reaction and cooled to room temperature. The coated substrates were washed with hot water for at least 6 hours, then calcined at 500° C. for 6 hours in air. The heating rate was controlled at 10° C. hour.

3. Analysis

The resulting membranes were characterized by x-ray diffraction, electron microscopy and permeability measurement.

Results and Discussion

1. Products

The following table shows some typical examples synthesized under different experimental conditions, such as reaction time, and substrate.

TABLE 1

| Sample | @ Substrate | Pore Size um | Reaction Temp °C. | Reaction Time Hrs. | Zeolite Layer Thickness $\mu$m | Result |
| --- | --- | --- | --- | --- | --- | --- |
| 1 | alumina | 0.08 | 180 | 4 | 4 | CPO MFI |
| 2 | alumina | 0.08 | 180 | 8 | 12 | CPO MFI |
| 3 | alumina | 0.08 | 180 | 18 | 30 | CPO MFI |
| 4 | SS | 0.25 | 180 | 4 | 4 | CPO MFI |
| 5 | SS | 0.25 | 180 | 8 | 11 | CPO MFI |
| 6 | SS | 0.25 | 180 | 20 | 30 | CPO MFI |
| 7 | alumina | 0.08 | 158 | 64 | 45 | CPO MFI |
| 8 | alumina | 1.0 | 158 | 64 | 45–50 | CPO MFI |
| 9 | SS | 0.25 | 158 | 64 | 50 | CPO MFI |
| 10 | SS | 2.0 | 158 | 64 | 50 | CPO MFI |

@ alumina: 0.08 $\mu$m and 1 $\mu$m pore size; SS = stainless steel, Pall Corporation, PMM Grade M020 (2 $\mu$m) and Mott Corp. (0.25)
CPO - Crystallographic Preferred Orientation.

What is claimed is:

1. A zeolite membrane comprising a substrate and a layer of zeolite crystals wherein said layer of zeolite crystals is a polycrystalline layer with at least 99% of said zeolite crystals having at least one point between adjacent crystals that is ≦20 Å and wherein at least 90% of said crystals have widths of from about 2 to about 50 microns and wherein at least 75% of said crystals have a thickness within 20% of the average crystal thickness and wherein said membrane has at most 1 V % voids in said zeolite layer, and wherein said substrate is selected from the group consisting of porous and non-porous substrates.

2. A zeolite membrane according to claim 1 wherein when said substrate is a porous substrate said porous substrate is selected from the group consisting of stainless steel, alumina, courdierite, mullite, titania, pyrex, silica, silicon nitride, silicon carbide, carbon, graphite and mixtures thereof.

3. A zeolite membrane according to claim 1 wherein said zeolite crystals are about 5 to about 100μ thick.

4. A zeolite membrane according to claim 1 wherein when said substrate is a non-porous substrate said substrate is selected from the group consisting of quartz, glass, borosilicate glasses, clay, metal, silicon, polymer, graphite, dense ceramic and mixtures thereof.

5. A zeolite membrane according to claim 1 wherein when said layer of zeolite crystals are MFI crystals said zeolite crystals have a C-orientation within 30° of the normal to the surface of said substrate.

6. A zeolite membrane according to claim 2 wherein said substrate has a porosity of about 5 to about 70% and a pore size distribution of about 0.004 to 100μ.

7. A zeolite membrane according to claim 1 wherein said substrate has an average roughness with an amplitude of less than 10 μm with an aspect ratio of the roughness less than 1:1.

8. A zeolite membrane according to claim 1 wherein said zeolite is selected from the group consisting of silicates, aluminosilicates, aluminophosphates, silicoaluminophosphates, metalloaluminophosphates, stanosilicates and mixtures thereof.

9. A zeolite membrane according to claim 8 wherein said layer of zeolite crystals is selected from the group consisting of MFI, FAU, zeolite y, zeolite x, MAZ, LTA, CHA, AFI, AEL, BEA, EUO, FER, KFI, MOR, MEL, MTW, OFF, TON, AFS, AFY, APC, APD, MTN, MTT, AEL and mixtures thereof.

10. A zeolite membrane according to claim 9 wherein said layer of zeolite crystals is a layer of MFI zeolite crystals.

11. A zeolite membrane according to claim 1 wherein said membrane has less than 0.5 V % voids.

12. A zeolite membrane according to claim 1 wherein said membrane has less than 10,000 defects of greater than 40 Å per square inch.

13. A zeolite membrane according to claim 1 wherein said zeolite layer has zeolite crystals of about 5 to about 100 μm.

14. A method for preparing a zeolite membrane, comprising the steps of:
(a) immersing a substrate onto which a zeolite layer is to be grown, in a zeolite synthesis mixture;
(b) autoclaving said substrate immersed in said zeolite synthesis mixture for a time and at a temperature sufficient to form a zeolite layer on said substrate, said substrate being oriented so that settling of particles produced from said zeolite synthesis mixture, during said autoclaving, onto said zeolite layer is prevented;
(c) washing said substrate and zeolite layer with a solution comprising water for a time and at a temperature sufficient to remove any unreacted zeolite synthesis mixture and to form a membrane, said membrane comprising a layer of zeolite crystals with at least 99% of said crystals having at least one point between adjacent crystals that is ≦20 Å and wherein at least 90% of said crystals have widths of from about 2 to about 50 microns and wherein at least 75% of said crystals have a thickness within 20% of the average crystal thickness and wherein said membrane has at most 1 V % voids in said zeolite layer, and wherein said substrate is selected from the group consisting of porous and non-porous substrates.

15. A method according to claim 14 wherein said membrane is calcined at a temperature of 400° to 600° C. for at least 30 minutes when said zeolite synthesis mixture contains an organic template.

16. A method according to claim 14 wherein said substrate is oriented such that said zeolite layer is grown on the side of the substrate oriented from 90 to 270 degrees in the synthesis mixture, and wherein in the 180 degree orientation, the zeolite layer is grown on the horizontal downward facing side.

17. A zeolite membrane according to claim 1 wherein said membrane has incorporated therein about 0.1 to about 10 wt % noble metal.

* * * * *